US012616671B2

(12) United States Patent
Reddy et al.

(10) Patent No.: US 12,616,671 B2
(45) Date of Patent: May 5, 2026

(54) USE OF RIGOSERTIB TO TREAT RNA VIRUS INFECTIONS

(71) Applicant: Icahn School of Medicine at Mount Sinai, New York, NY (US)

(72) Inventors: Premkumar Reddy, New York, NY (US); Kris White, New York, NY (US); M.V. Ramana Reddy, New York, NY (US); Adolfo Garcia-Sastre, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 578 days.

(21) Appl. No.: 17/927,978

(22) PCT Filed: May 28, 2021

(86) PCT No.: PCT/US2021/034772
§ 371 (c)(1),
(2) Date: Nov. 28, 2022

(87) PCT Pub. No.: WO2021/243162
PCT Pub. Date: Dec. 2, 2021

(65) Prior Publication Data
US 2023/0248680 A1     Aug. 10, 2023

Related U.S. Application Data

(60) Provisional application No. 63/032,300, filed on May 29, 2020.

(51) Int. Cl.
*A61K 31/198*     (2006.01)
*A61P 31/14*     (2006.01)

(52) U.S. Cl.
CPC ............ *A61K 31/198* (2013.01); *A61P 31/14* (2018.01)

(58) Field of Classification Search
CPC .............................. A61K 31/198; A61P 31/14
See application file for complete search history.

(56) References Cited

U.S. PATENT DOCUMENTS

| | | | |
|---|---|---|---|
| 7,598,232 B2 | 10/2009 | Reddy et al. | |
| 8,664,272 B2 | 3/2014 | Reddy et al. | |
| 9,242,945 B2 | 1/2016 | Reddy et al. | |
| 2014/0086941 A1 | 3/2014 | Reddy et al. | |
| 2018/0071293 A1 | 3/2018 | Buggy et al. | |

(Continued)

FOREIGN PATENT DOCUMENTS

| | | |
|---|---|---|
| WO | WO 2003/072062 | 9/2003 |
| WO | WO 2012/166586 | 12/2012 |
| WO | WO 2014/031571 | 2/2014 |

(Continued)

OTHER PUBLICATIONS

Daga et al. J. Adv. Res. Med. 2019; 6(4) (Year: 2019).*

(Continued)

*Primary Examiner* — Brandon J Fetterolf
(74) *Attorney, Agent, or Firm* — Fish & Richardson P.C.

(57)     ABSTRACT

Provided herein are methods for treating a virus (e.g,. an RNA virus, such as a SARS-CoV-2) infection or a disease associated therewith (e.g., COVID-19) comprising administering Rigosertib or a composition thereof to a subject (e.g., a human subject).

4 Claims, 2 Drawing Sheets

Rigosertib

(56) References Cited

U.S. PATENT DOCUMENTS

Figures 2A, 2B, 2C:
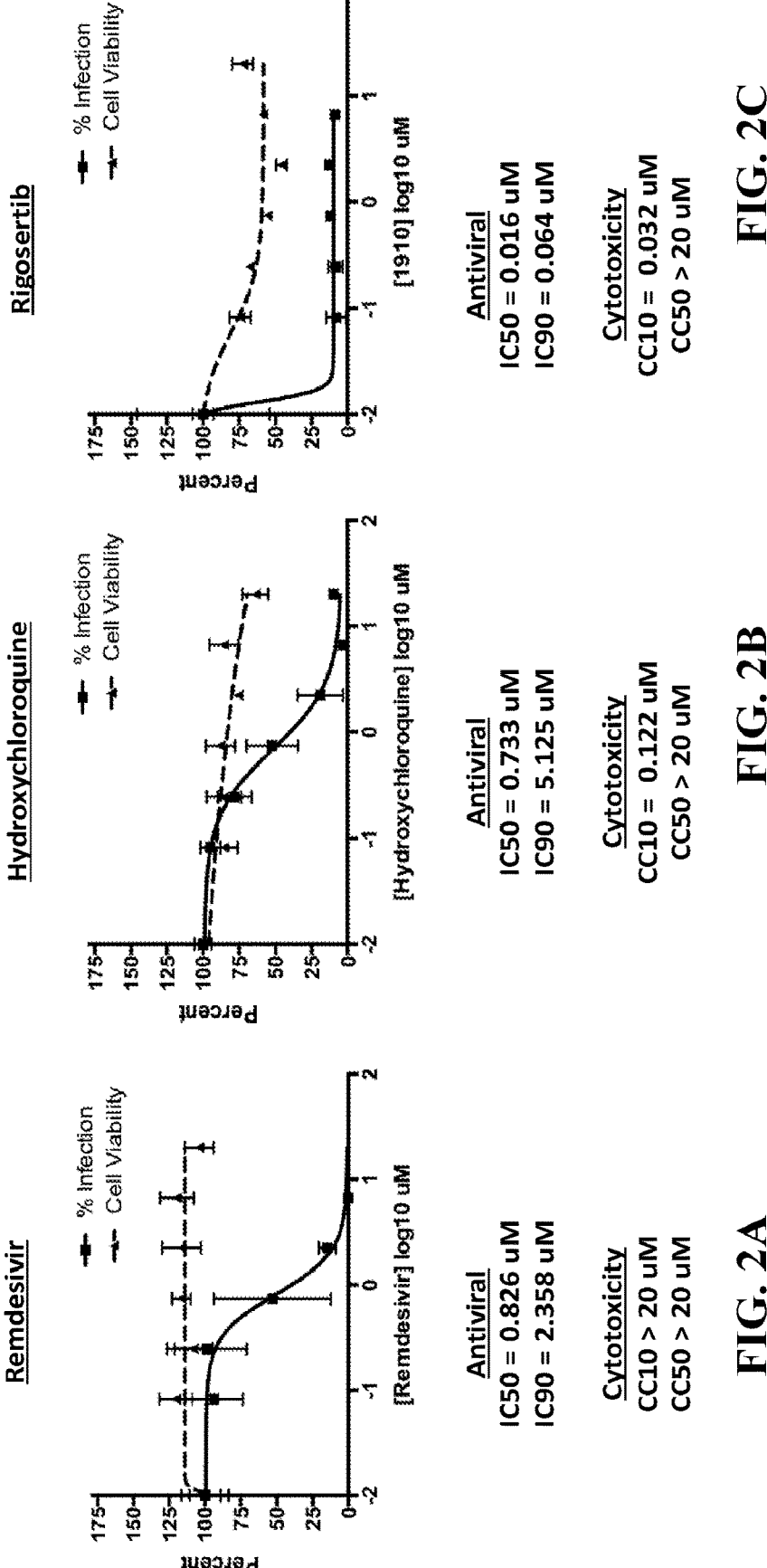

2023/0286934 A1 9/2023 Reddy et al.

FOREIGN PATENT DOCUMENTS

WO    WO 2018/169283        9/2018
WO    WO 2018/169283 A1 *   9/2018

OTHER PUBLICATIONS

Pohl et al. (Scientific Reports (2017) 7:8629, IDS) (Year: 2017).*
Extended European Search Report in European Appln. No. 21812448.
5, mailed on May 28, 2024, 7 pages.
Guo et al., "Identification of 1-9 Repurposal Drugs and Adverse
Drug Reactions for Various Courses of Coronavirus Disease 2019
(COVID-19) Based on Single-cell RNA Sequencing Data," Arxiv.
org, Cornell University Library, May 16, 2020, 26 pages.
Supplementary European Search Report in European U.S. Appl. No.
21/822,105, mailed on Jun. 4, 2024, 8 pages.
Xiang et al., "Glucocorticoids improve severe or critical COVID-19
by activating ACE2 and reducing IL-6 levels," International Journal
of Biological Sciences, Jan. 1, 2020, 16(13):2382-2391.
[No Author], "Onconova Therapeutics Submits Application for
Rigosertib to Participate in Federally Funded Human Studies in
COVID-19 Disease," SymBio Pharmaceuticals Limited, Jul. 2020,
2 pages.
Athuluri-Divakar et al., "A Small Molecule RAS-Mimetic Disrupts
RAS Association with Effector Proteins to Block Signaling," Cell,
Apr. 2016, 165(3):643-655.
Gordon et al., "A SARS-CoV-2 protein interaction map reveals
targets for drug repurposing," Nature, Apr. 2020, 583(7816):459-
468.
Hummel et al., "Epstein-Barr virus RNA. VIII. Viral RNA in
permissively infected B95-8 cells" Journal of Virology, Jul. 1982,
41(1)262-272.
International Preliminary Report on Patentability in International
Appln. No. PCT/US2021/036407, mailed on Dec. 13, 2022, 9
pages.
International Preliminary Report on Patentability in International
Appln. No. PCT/US2021/034772, mailed on Dec. 22, 2022, 6
pages.
International Search Report and Written Opinion in International
Appln. No. PCT/US2021/036407, mailed on Sep. 28, 2017, 10
pages.
International Search Report and Written Opinion in International
Appln. No. PCT/US2021/034772, mailed on Aug. 23, 2021, 7
pages.
Pohl et al., "Identification of Polo-like kinases as potential novel
drug targets for influenza A virus," Scientific Reports, Aug. 2017,
7(1):1-11.
Reed et al., "A simple method of estimating fifty percent endpoint,"
The American Journal of Hygiene, May 1938, 27(3):493-497.
Roschewski et al., "Phase I study of ON 01910.Na (Rigosertib), a
multikinase PI3K inhibitor in relapsed/refractory B-cell malignan-
cies," Leukemia, Sep. 2013, 27(9):1920-1923.
Xiang et al., "Glucocorticoids improve severe or critical COVID-19
by activating ACE2 and reducing IL-6 levels," International Journal
of Biological Sciences, Jun. 27, 2020, 16(13):2382-2391.

* cited by examiner

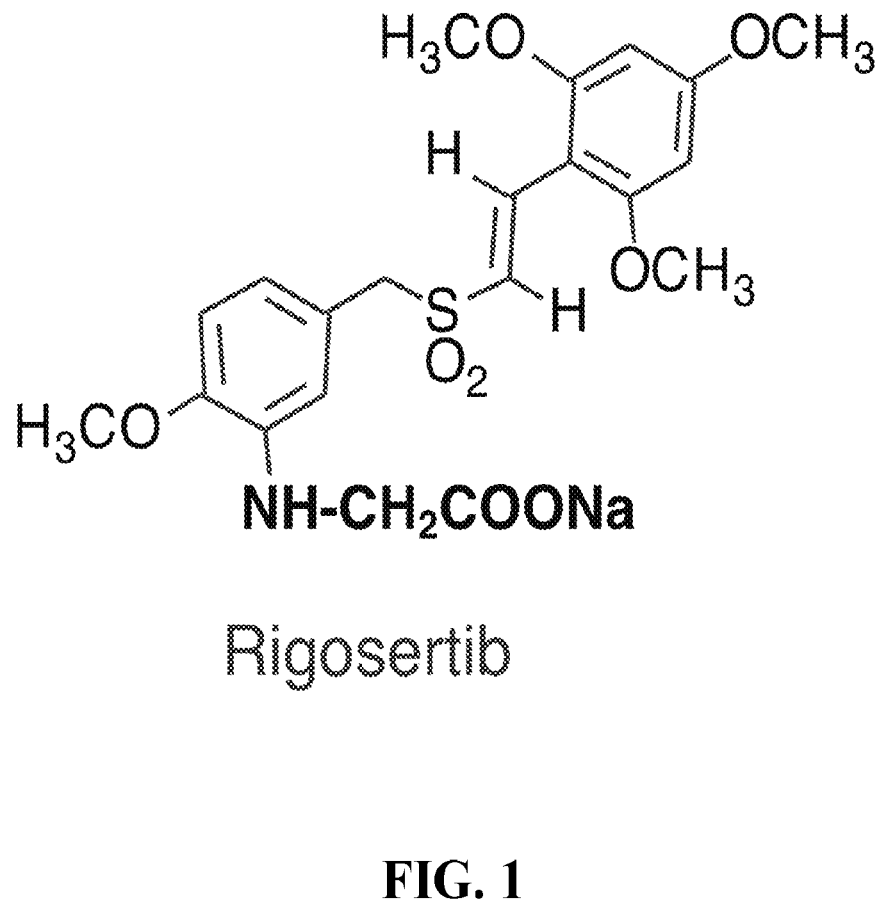

Rigosertib

FIG. 1

USE OF RIGOSERTIB TO TREAT RNA VIRUS INFECTIONS

FEDERALLY SPONSORED RESEARCH OR DEVELOPMENT

This invention was made with government support under HHSN272201400008C and U19AI135972 awarded by the NIAID and NIH. The government has certain rights in the invention.

FIELD OF THE INVENTION

The present invention relates to compositions and methods for treating RNA virus infections or diseases associated therewith. More particularly, the present invention is directed to the treatment of SARS-CoV-2 and other viral infections by administration of rigosertib.

1. BACKGROUND

There is an urgent need to develop therapeutics to treat COVID-19 and diagnostics to detect severe acute respiratory syndrome coronavirus-2 (SARS-CoV-2). As of May 26 2020, more than 5,550,399 people globally have tested positive for SARS-CoV-2. In addition, as of May 26, 2020, globally more than 348,302 people have died from COVID-19. Currently, there is no approved vaccine or therapeutic to prevent or treat COVID-19.

Rigosertib (otherwise known as ON01910. Na) is a synthetic benzyl styryl sulfone substance, previously developed as an anticancer agent, and has recently completed Phase III clinical trials for the treatment of Myelodysplastic Syndrome (MDS). (See U.S. Pat. No. 7,598,232), myelodysplastic syndrome and acute myeloid leukemia (U.S. Pat. No. 8,664,272). Rigosertib is a small molecule RAS-mimetic that suppresses RAS-mediated signaling pathways (Athuluri-Divakar et al., A Small Molecule RAS-Mimetic Disrupts RAS Association with Effector Proteins to Block Signaling. *Cell*. 2016; 165(3):643-655. doi:10.1016/j.cell.2016.03.045) and thus acts as a suppressor of multiple cellular signaling pathways. Rigosertib is a water-soluble compound that is orally bio-available with little or no toxic side effects and has been used to treat over 1000 patients in clinical trials. Thus, its Absorption, Distribution, Metabolism, Excretion and Toxicity profiles in human subjects is well established.

Drug repurposing is aimed at developing new indications for drugs currently in use and is recognized as an important approach to rapidly develop new treatments for unrelated diseases. This approach of drug repurposing reduces the cost and duration of new drug development since the safety profile of the compound is well established from earlier clinical trials. Drug repurposing has the following advantages: (1) the use, preparation and stability of the drug candidate established; (2) Absorption, Distribution, Metabolism, Excretion and Toxicity (ADMET), are established; (3) the probability of failure due to safety issues is significantly lower because of the available clinical trial data; (4) Time required for Post-marketing Surveillance (PMS) is greatly diminished.

2. SUMMARY

In one aspect, provided herein is the use of Rigosertib as an antiviral (e.g., an antiviral for RNA virus infections). The use of Rigosertib as an antiviral is based, in part, on the discovery that it inhibits the replication of SARS-CoV-2, a positive-sense single-stranded RNA virus. See Section 5, infra. RNA viruses utilize cellular signaling machinery for their replication and virus assembly, suggesting that inhibition of one or more of these signaling pathways could result in the inhibition of viral replication. For example, SARS-CoV-2 infection is initiated by the interaction of viral spike protein with host cell surface receptors such as Angiotensin-converting enzyme 2 (ACE2) or CD147. This event results in the fusion of cellular and viral membranes leading to the release of viral genome into the cellular cytoplasm. Infection of lung epithelial cells with SARS-CoV-2 induces the activation of multiple signaling pathways leading to enhanced replication of the virus as well as several pathogenic events associated with coronavirus infection (Gordon et al., 2020, A SARS-CoV-2 protein interaction map reveals targets for drug repurposing [published online ahead of print, 2020 Apr. 30]. Nature. 2020; 10.1038/s41586-020-2286-9. doi: 10.1038/s41586-020-2286-9). Rigosertib is a small molecule RAS-mimetic that suppresses RAS-mediated signaling pathways (Athuluri-Divakar et al., A Small Molecule RAS-Mimetic Disrupts RAS Association with Effector Proteins to Block Signaling. *Cell*. 2016; 165(3):643-655. doi: 10.1016/j.cell.2016.03.045) and thus acts as a suppressor of multiple cellular signaling pathways. Since mutations in the viral genome do not have an effect on cellular signaling machinery, the use of Rigosertib as an antiviral avoids development of resistance to the drug as a result of mutations in the virus.

In another aspect, provided herein are methods for treating a virus infection or a disease associated therewith, comprising administering Rigosertib to a subject in need thereof. In one embodiment, provided herein is a method for treating an RNA virus infection or a disease associated therewith comprising administering Rigosertib to a subject in need thereof. The RNA virus may be single stranded or double-stranded, positive or negative sense, and segmented or non-segmented. In some embodiments, the RNA virus is a single-stranded, positive sense RNA virus. In other embodiments, the RNA virus is a single-stranded, negative sense segmented or non-segmented virus. In a specific embodiment, the RNA virus is a coronavirus (e.g., SARS-CoV-1 or SARS-CoV-2), an influenza virus (e.g., an influena A virus or an influenza B virus), hepatitis C virus, vesicular stomatitis virus (VSV) or Newcastle disease virus (NDV). In a particular embodiment, provided herein is a method for treating a SARS-CoV-2 infection or COVID-19, comprising administering Rigosertib to a subject in need thereof. Rigosertib may be provided in any acceptable format for veterinary or human administration.

In another embodiment, provided herein is a method for treating a virus infection or a disease associated therewith, comprising administering an effective amount of Rigosertib to a subject in need thereof. In another embodiment, provided herein is a method for treating an RNA virus infection or a disease associated therewith, comprising administering an effective amount of Rigosertib to a subject in need thereof. The RNA virus may be single stranded or double-stranded, positive or negative sense, and segmented or non-segmented. In some embodiments, the RNA virus is a single-stranded, positive sense RNA virus. In other embodiments, the RNA virus is a single-stranded, negative sense segmented or non-segmented virus. In a specific embodiment, the RNA virus is a coronavirus (e.g., SARS-CoV-1 or SARS-CoV-2), an influenza virus (e.g., an influena A virus or an influenza B virus), heptatitis C virus, vesicular stomatitis virus (VSV) or Newcastle disease virus (NDV). In a particular embodiment, provided herein is a method for treating a SARS-CoV-2 infection or COVID-19, comprising administering an effective amount of Rigosertib to a subject in need thereof.

In another embodiment, provided herein is a method for treating a virus infection or a disease associated therewith, comprising administering a pharmaceutical composition comprising an effective amount of Rigosertib to a subject in need thereof. In another embodiment, provided herein is a method for treating an RNA virus infection or a disease associated therewith, comprising administering a pharmaceutical composition comprising an effective amount of Rigosertib to a subject in need thereof. The RNA virus may be single stranded or double-stranded, positive or negative sense, and segmented or non-segmented. In some embodiments, the RNA virus is a single-stranded, positive sense RNA virus. In other embodiments, the RNA virus is a single-stranded, negative sense segmented or non-segmented virus. In a specific embodiment, the RNA virus is a coronavirus (e.g., SARS-CoV-1 or SARS-CoV-2), an influenza virus (e.g., an influena A virus or an influenza B virus), hepatitis C virus, vesicular stomatitis virus (VSV) or Newcastle disease virus (NDV). In a particular embodiment, provided herein is a method for treating a SARS-CoV-2 infection or COVID-19, comprising administering a pharmaceutical composition comprising an effective amount of Rigosertib to a subject in need thereof.

In another aspect, provided herein are methods for preventing a disease associated with a virus infection, comprising administering Rigosertib to a subject in need thereof. In one embodiment, provided herein is a method for treating or preventing a disease associated with an RNA virus infection, comprising administering Rigosertib to a subject in need thereof. The RNA virus may be single stranded or double-stranded, positive or negative sense, and segmented or non-segmented. In some embodiments, the RNA virus is a single-stranded, positive sense RNA virus. In other embodiments, the RNA virus is a single-stranded, negative sense segmented or non-segmented virus. In a specific embodiment, the RNA virus is a coronavirus (e.g., SARS-CoV-1 or SARS-CoV-2), an influenza virus (e.g., an influena A virus or an influenza B virus), hepatitis C virus, vesicular stomatitis virus (VSV) or Newcastle disease virus (NDV). In a particular embodiment, provided herein is a method for preventing COVID-19, comprising administering Rigosertib to a subject in need thereof. Rigosertib may be provided in any acceptable format for veterinary or human administration.

In another embodiment, provided herein is a method for preventing a disease associated with a virus infection, comprising administering an effective amount of Rigosertib to a subject in need thereof. In another embodiment, provided herein is a method for preventing a disease associated with an RNA virus infection, comprising administering an effective amount of Rigosertib to a subject in need thereof. The RNA virus may be single stranded or double-stranded, positive or negative sense, and segmented or non-segmented. In some embodiments, the RNA virus is a single-stranded, positive sense RNA virus. In other embodiments, the RNA virus is a single-stranded, negative sense segmented or non-segmented virus. In a specific embodiment, the RNA virus is a coronavirus (e.g., SARS-CoV-1 or SARS-CoV-2), an influenza virus (e.g., an influena A virus or an influenza B virus), hepatitis C virus, vesicular stomatitis virus (VSV) or Newcastle disease virus (NDV). In a particular embodiment, provided herein is a method for preventing COVID-19, comprising administering an effective amount of Rigosertib to a subject in need thereof.

In another embodiment, provided herein is a method for preventing a disease associated with a virus infection, comprising administering a pharmaceutical composition comprising an effective amount of Rigosertib to a subject in need thereof. In another embodiment, provided herein is a method for preventing a disease associated with an RNA virus infection, comprising administering a pharmaceutical composition comprising an effective amount of Rigosertib to a subject in need thereof. The RNA virus may be single stranded or double-stranded, positive or negative sense, and segmented or non-segmented. In some embodiments, the RNA virus is a single-stranded, positive sense RNA virus. In other embodiments, the RNA virus is a single-stranded, negative sense segmented or non-segmented virus. In a specific embodiment, the RNA virus is a coronavirus (e.g., SARS-CoV-1 or SARS-CoV-2), an influenza virus (e.g., an influena A virus or an influenza B virus), hepatitis C virus, vesicular stomatitis virus (VSV) or Newcastle disease virus (NDV). In a particular embodiment, provided herein is a method for preventing COVID-19, comprising administering a pharmaceutical composition comprising an effective amount of Rigosertib to a subject in need thereof.

3. DESCRIPTION OF THE FIGURES

FIG. 1. Structure of Rigosertib.

FIGS. 2A-2C. Effect of Remdesevir (FIG. 2A), Hydroxychloroquine (FIG. 2B), and Rigosertib (FIG. 2C) on COVID-19 replication and cell viability.

4. DETAILED DESCRIPTION

4.1 Compositions

Provided herein are compositions (e.g., pharmaceutical compositions) comprising Rigosertib having the desired degree of purity in a pharmaceutically acceptable carrier, excipient or stabilizer (*Remington's Pharmaceutical Sciences* (1990) Mack Publishing Co., Easton, PA). Rigosertib may be produced using any technique known to one of skill (such as, e.g., described in U.S. Pat. No. 7,598,232 or International Patent Application Publication No. WO 03/072062 A2). In a specific embodiment, a composition comprises Rigosertib and an acceptable carrier or excipient. Examples of pharmaceutical compositions (or preparations) of Rigosertib that may be used are described in U.S. Pat. Nos. 7,598,232, 8,664,272, and International Patent Application Publication No. WO 03/072062 A2.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN®80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

A pharmaceutical composition may be formulated for any route of administration to a subject. Specific examples of routes of administration include oral, intransal, transdermal, intradermal, parenteral, and mucosal. In a specific embodiment, the composition is formulated for oral administration. In another specific embodiment, the composition is formulated for intramuscular or intravenous administration. Parenteral administration, characterized by either subcutaneous, intramuscular or intravenous injection, is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol.

In certain embodiments, Rigosertib is administered in a tablet, capsule or other oral formulation. In embodiments, Rigosertib is administered in a pharmaceutical composition known to one of skill in the art. A pharmaceutical composition comprising Rigosertib may be used to treat a virus (e.g., an RNA virus) infection or disease associated therewith. A pharmaceutical composition comprising Rigosertib may also be used to prevent a disease associated with a virus (e.g., an RNA virus) infection. In a specific embodiment, a pharmaceutical composition comprising Rigosertib is used to treat a SARS-CoV-2 infection or COVID-19. In another specific embodiment, a pharmaceutical composition comprising Rigosertib is used to prevent COVID-19.

4.2 Prophylactic and Therapeutic Uses of Rigosertib

In one aspect, provided herein are methods for treating a virus infection or disease associated therewith comprising administering Rigosertib to a subject in need thereof. In a specific embodiment, provided herein is a method for treating a virus infection or disease associated therewith in a subject comprising administering to the subject an effective amount of Rigosertib. In another specific embodiment, provided herein is a method for treating a virus infection or disease associated therewith in a subject comprising administering to the subject a pharmaceutical composition comprising an effective amount of Rigosertib. In another specific embodiment, provided herein is a method for treating a virus infection or disease associated therewith comprising administering to the subject an effective amount of Rigosertib and another therapy, such as known to one of skill in the art or described herein. In another specific embodiment, provided herein is a method for treating a virus infection or disease associated therewith in a subject comprising administering to the subject a pharmaceutical composition comprising an effective amount of Rigosertib, and another therapy, such as known to one of skill in the art or described herein (see, e.g., Section 4.2.2).

In another aspect, provided herein are methods for treating an RNA virus infection or disease associated therewith comprising administering Rigosertib to a subject in need thereof. In a specific embodiment, provided herein is a method for treating an RNA virus infection or disease associated therewith in a subject comprising administering to the subject an effective amount of Rigosertib. In another specific embodiment, provided herein is a method for treating an RNA virus infection or disease associated therewith in a subject comprising administering to the subject a pharmaceutical composition comprising an effective amount of Rigosertib. In another specific embodiment, provided herein is a method for treating an RNA virus infection or disease associated therewith comprising administering to the subject an effective amount of Rigosertib and another therapy, such as known to one of skill in the art or described herein. In another specific embodiment, provided herein is a method for treating an RNA virus infection or disease associated therewith in a subject comprising administering to the subject a pharmaceutical composition comprising an effective amount of Rigosertib, and another therapy, such as known to one of skill in the art or described herein (see, e.g., Section 4.2.2).

In another aspect, provided herein are methods for preventing a disease associated with a virus infection comprising administering Rigosertib to a subject in need thereof. In a specific embodiment, provided herein is a method for treating preventing a disease associated with a virus infection in a subject comprising administering to the subject an effective amount of Rigosertib. In another specific embodiment, provided herein is a method for preventing a disease associated with a virus infection in a subject comprising administering to the subject a pharmaceutical composition comprising an effective amount of Rigosertib. In another specific embodiment, provided herein is a method for preventing a disease associated with a virus infection comprising administering to the subject an effective amount of Rigosertib and another therapy, such as known to one of skill in the art or described herein. In another specific embodiment, provided herein is a method for preventing a disease associated with a virus infection in a subject comprising administering to the subject a pharmaceutical composition comprising an effective amount of Rigosertib, and another therapy, such as known to one of skill in the art or described herein (see, e.g., Section 4.2.2).

In another aspect, provided herein are methods for preventing a disease associated with an RNA virus infection comprising administering Rigosertib to a subject in need thereof. In a specific embodiment, provided herein is a method for treating an RNA virus infection or disease associated therewith in a subject comprising administering to the subject an effective amount of Rigosertib. In another specific embodiment, provided herein is a method for preventing a disease associated with an RNA virus infection in a subject comprising administering to the subject a pharmaceutical composition comprising an effective amount of Rigosertib. In another specific embodiment, provided herein is a method for preventing a disease associated with an RNA virus infection comprising administering to the subject an effective amount of Rigosertib and another therapy, such as known to one of skill in the art or described herein. In another specific embodiment, provided herein is a method for preventing a disease associated with an RNA virus infection in a subject comprising administering to the subject a pharmaceutical composition comprising an effective amount of Rigosertib, and another therapy, such as known to one of skill in the art or described herein (see, e.g., Section 4.2.2).

The RNA virus may be single stranded or double-stranded, positive or negative sense, and segmented or non-segmented. In some embodiments, the RNA virus is a single-stranded, positive sense RNA virus. In other embodiments, the RNA virus is a single-stranded, negative sense segmented or non-segmented virus. In a specific embodiment, the RNA virus is a coronavirus (e.g., SARS-CoV-1 or SARS-CoV-2), an influenza virus (e.g., an influena A virus or an influenza B virus), heptatitis C virus, vesicular stomatitis virus (VSV) or Newcastle disease virus (NDV).

In a particular embodiment, the administration of an effective amount of Rigosertib to the subject inhibits or reduces in the progression of a disease associated with a virus (e.g., an RNA virus). In another embodiment, the administration of an effective amount of Rigosertib to the subject inhibits or reduces onset, development and/or severity of a symptom thereof (e.g., fever, myalgia, cough, difficulty breathing, tiredness) of a virus (e.g., an RNA virus) infection or disease associated therewith. In another embodiment, the administration of an effective amount of Rigosertib to the subject inhibits or reduces duration of a virus (e.g., an RNA virus) infection, or disease or a symptom associated therewith. In another embodiment, the administration of an effective amount of Rigosertib to the subject reduces organ failure associated with a virus (e.g., an RNA virus) infection or disease associated therewith. In another embodiment, the administration of an effective amount of Rigosertib to the subject reduces the hospitalization of the subject. In another embodiment, the administration of an effective amount of Rigosertib to the subject reduces the length of hospitalization of the subject. In another embodiment, the administration of an effective amount of Rigosertib to the subject increases the overall survival of subjects with a virus (e.g., an RNA virus) infection or disease associated therewith. In another embodiment, the administration of an effective amount of Rigosertib to the subject prevents the onset or progression of a secondary infection associated with virus (e.g., RNA virus) infection.

In a specific embodiment, administration of Rigosertib to a subject reduces the incidence of hospitalization by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the incidence of hospitalization in the absence of administration of Rigosertib.

In a specific embodiment, administration of Rigosertib to a subject reduces mortality by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the mortality in the absence of administration of Rigosertib.

In certain embodiments, the administration of an effective amount of Rigosertib to a subject results in one, two, three, four, five, or more of the following effects: (i) reduction or amelioration in the severity of a virus (e.g., an RNA virus) infection, or a disease or a symptom associated therewith; (ii) reduction in the duration of a virus (e.g., an RNA virus) infection, or a disease or a symptom associated therewith; (iii) prevention of the progression of a virus (e.g., an RNA virus) infection, or a disease or a symptom associated therewith; (iv) regression of a virus (e.g., an RNA virus) infection, or a disease or a symptom associated therewith; (v) prevention of the development or onset of a symptom of a virus (e.g., an RNA virus) infection or a disease associated therewith; (vi) reduction in organ failure associated with a SARS-CoV-2 infection or COVID-19; (vii) reduction in the hospitalization of a subject; (viii) reduction in the hospitalization length; (ix) an increase in the survival of a subject with a virus (e.g., an RNA virus) infection or a disease associated therewith; (x) reduction in virus (e.g., RNA virus) titer; (xi) the reduction in the number of symptoms associated with a virus (e.g., an RNA virus) infection or a disease associated therewith; (xiii) inhibits replication of the virus (e.g., RNA virus); (xiv) enhancement, improvement, supplementation, complementation, or augmentation of the prophylactic or therapeutic effect(s) of another therapy; (xii) prevention of the onset or progression of a secondary infection associated with a virus (e.g., RNA virus) infection; and/or (xiii) prevention of the onset or diminution of disease severity of bacterial infection occurring secondary to a virus (e.g., RNA virus) infection.

In a specific aspect, provided herein are methods for treating a SARS-CoV-2 infection or COVID-19 comprising administering Rigosertib to a subject in need thereof. In a specific embodiment, provided herein is a method for treating a SARS-CoV-2 infection or COVID-19 in a subject comprising administering to the subject an effective amount of Rigosertib. In another specific embodiment, provided herein is a method for treating a SARS-CoV-2 infection or COVID-19 in a subject comprising administering to the subject a pharmaceutical composition comprising an effective amount of Rigosertib. In another specific embodiment, provided herein is a method for treating a SARS-CoV-2 infection or COVID-19 comprising administering to the subject an effective amount of Rigosertib and another therapy, such as known to one of skill in the art or described herein. In another specific embodiment, provided herein is a method for treating a SARS-CoV-2 infection or COVID-19 in a subject comprising administering to the subject a pharmaceutical composition comprising an effective amount of Rigosertib, and another therapy, such as known to one of skill in the art or described herein (see, e.g., Section 4.2.2).

In another specific aspect, provided herein are methods for preventing COVID-19 comprising administering Rigosertib to a subject in need thereof. In a specific embodiment, provided herein is a method for preventing COVID-19 in a subject comprising administering to the subject an effective amount of Rigosertib. In another specific embodiment, provided herein is a method for preventing COVID-19 in a subject comprising administering to the subject a pharmaceutical composition comprising an effective amount of Rigosertib. In another specific embodiment, provided herein is a method for preventing COVID-19 comprising administering to the subject an effective amount of Rigosertib and another therapy, such as known to one of skill in the art or described herein. In another specific embodiment, provided herein is a method for preventing COVID-19 in a subject comprising administering to the subject a pharmaceutical composition comprising an effective amount of Rigosertib, and another therapy, such as known to one of skill in the art or described herein (see, e.g., Section 4.2.2).

In a particular embodiment, the administration of an effective amount of Rigosertib to the subject inhibits or reduces in the progression of COVID-19. In another embodiment, the administration of an effective amount of Rigosertib to the subject inhibits or reduces onset, development and/or severity of a symptom thereof (e.g., fever, myalgia, cough, difficulty breathing, tiredness) of COVID-19. In another embodiment, the administration of an effective amount of Rigosertib to the subject inhibits or reduces duration of COVID-19 or a symptom associated therewith. In another embodiment, the administration of an effective amount of Rigosertib to the subject reduces organ failure associated with COVID-19. In another embodiment, the administration of an effective amount of Rigosertib to the subject reduces the hospitalization of the subject. In another embodiment, the administration of an effective amount of Rigosertib to the subject reduces the length of hospitalization of the subject. In another embodiment, the administration of an effective amount of Rigosertib to the subject increases the overall survival of subjects with COVID-19. In another embodiment, the administration of an effective amount of Rigosertib to the subject prevents the onset or progression of a secondary infection associated with SARS-CoV-2 infection.

In a specific embodiment, administration of Rigosertib to a subject reduces the incidence of hospitalization by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the incidence of hospitalization in the absence of administration of Rigosertib.

In a specific embodiment, administration of Rigosertib to a subject reduces mortality by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the mortality in the absence of administration of Rigosertib.

In certain embodiments, the administration of an effective amount of Rigosertib to a subject results in one, two, three, four, five, or more of the following effects: (i) reduction or amelioration in the severity of a SARS-CoV-2 infection, COVID-19 or a symptom associated therewith; (ii) reduction in the duration of a SARS-CoV-2 infection, COVID-19 or a symptom associated therewith; (iii) prevention of the progression of a SARS-CoV-2 infection, COVID-19 or a symptom associated therewith; (iv) regression of a SARS-CoV-2 infection, COVID-19 or a symptom associated therewith; (v) prevention of the development or onset of a symptom of a SARS-CoV-2 infection or COVID-19; (vi) reduction in organ failure associated with a SARS-CoV-2 infection or COVID-19; (vii) reduction in the hospitalization of a subject; (viii) reduction in the hospitalization length; (ix) an increase in the survival of a subject with a SARS-CoV-2 infection or COVID-19; (x) reduction in SARS-CoV-2 titer; (xi) the reduction in the number of symptoms associated with a SARS-CoV-2 infection or COVID-19; (xxiii) enhancement, improvement, supplementation, complementation, or augmentation of the prophylactic or therapeutic effect(s) of another therapy; (xii) prevention of the onset or progression of a secondary infection associated with a SARS-CoV-2 infection; and/or (xiii) prevention of the onset or diminution of disease severity of bacterial pneumonias occurring secondary to a SARS-CoV-2 infection.

In a specific embodiment, administration of Rigosertib to a subject reduces the number of and/or the frequency of symptoms of in the subject (exemplary symptoms of a SARS-CoV-2 include, but are not limited to, body aches (especially joints and throat), fever, nausea, headaches, fatigue, sore throat, and difficulty breathing). In another specific embodiment, administration of Rigosertib to a subject reduces the progression of a SARS-CoV-2 infection or COVID-19 using the WHO ordinal scale. In another specific embodiment, administration of Rigosertib to a subject reduces the need for invasive mechanical ventilation. In another specific embodiment, administration of Rigosertib to a subject reduces the need to provide oxygen supplementation to the subject. In another specific embodiment, administration of Rigosertib to a subject reduces the mortality caused by a SARS-CoV-2 infection or COVID-19.

Rigosertib may be administered alone or in combination with another/other type of therapy known in the art. See, e.g., Section 4.2.2 for other therapies.

In specific embodiment, Rigosertib may be used as any line of therapy, including, but not limited to, a first, second, third, fourth and/or fifth line of therapy.

4.2.1 Routes of Administration and Dosage

Rigosertib or composition described herein may be delivered to a subject by a variety of routes. These include, but are not limited to, oral, intradermal, intramuscular, intraperitoneal, transdermal, intravenous, intranasal and subcutaneous routes. In a specific embodiment, a route known to one of skill in the art is used to administer Rigosertib or composition thereof.

Exemplary dosages of Rigosertib are 280 mg 560 mg, 840 mg, and 1120 mg. In a specific embodiment, a dosage of Rigosertib or composition thereof known to one of skill in the art is used to treat a subject in accordance with the methods described herein. An exemplary treatment regime entails administration once or twice per day for a period of 7 days, 14 days, 28 days, 2 months, 3 months, or more. In another specific embodiment, administration is discontinued if the subject experiences an adverse event.

4.2.2 Combination Therapy

In various embodiments, Rigosertib or composition described herein may be administered to a subject in combination with one or more other therapies (e.g., antiviral or immunomodulatory therapies). In some embodiments, a pharmaceutical composition described herein may be administered to a subject in combination with one or more therapies. The one or more other therapies may be in the same composition or a different composition as Rigosertib.

In some embodiments, the one or more other therapies that are supportive measures, such as pain relievers, anti-fever medications, or therapies that alleviate or assist with breathing. Specific examples of supportive measures include humidification of the air by an ultrasonic nebulizer, aerolized racemic epinephrine, oral dexamethasone, intravenous fluids, intubation, fever reducers (e.g., ibuprofen, acetometaphin), and antibiotic and/or antifungal therapy (i.e., to prevent or treat secondary bacterial and/or fungal infections).

In certain embodiments, the therapies are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In some embodiments, two or more therapies are administered concurrently. The two or more therapies can be administered in the same composition or a different composition. Further, the two or more therapies can be administered by the same route of administration of a different route of administration.

4.2.3 Patient Populations

As used herein, the terms "subject" and "patient" are used interchangeably to refer to an animal (e.g., birds, reptiles, and mammals, such as humans). In one embodiment, a patient treated in accordance with the methods provided herein is a patient suffering from or expected to suffer from a virus (e.g., RNA virus) infection or a disease associated therewith. In another embodiment, a patient treated in accordance with the methods provided herein is a patient exposed to a virus (e.g., RNA virus) infection but not manifesting any symptoms of the infection or a disease associated therewith. In another embodiment, a patient treated in accordance with the methods provided herein is a patient experiencing one or more symptoms of a virus (e.g., RNA virus) infection or disease associated therewith. In another embodiment, a patient treated in accordance with the methods provided herein is a patient diagnosed with a virus (e.g., RNA virus) infection or a disease associated therewith. In some embodiments, a patient treated in accordance with the methods provided herein is a patient infected with a virus (e.g., RNA virus) infection that does not manifest any symptoms of the infection or a disease associated therewith. In certain embodiments, a patient treated in accordance with the methods provided herein is a patient infected with a virus (e.g., RNA virus) infection that manifests mild symptoms of the infection or a disease associated therewith. In some embodiments, a patient treated in accordance with the methods provided herein is a patient infected with a virus (e.g., RNA virus) infection that manifests moderate symptoms of the infection or a disease associated therewith. In certain embodiments, a patient treated in accordance with the methods provided herein is a patient infected with a virus (e.g., RNA virus) infection that manifests moderate to severe symptoms of the infection or a disease associated therewith.

In another embodiment, a patient treated in accordance with the methods provided herein is a patient suffering from or expected to suffer from a SARS-CoV-2 infection or COVID-19. In another embodiment, a patient treated in accordance with the methods provided herein is a patient exposed to a SARS-CoV-2 infection but not manifesting any symptoms of the infection or COVID-19. In another embodiment, a patient treated in accordance with the methods provided herein is a patient diagnosed with a SARS-CoV-2 infection or COVID-19. In some embodiments, a patient treated in accordance with the methods provided herein is a patient infected with a SARS-CoV-2 infection that does not manifest any symptoms of the infection or COVID-19. In certain embodiments, a patient treated in accordance with the methods provided herein is a patient infected with a SARS-CoV-2 infection that manifests mild symptoms of the infection or COVID-19. In some embodiments, a patient treated in accordance with the methods provided herein is a patient infected with a SARS-CoV-2 infection that manifests moderate symptoms of the infection or COVID-19. In certain embodiments, a patient treated in accordance with the methods provided herein is a patient infected with a SARS-CoV-2 infection that manifests moderate to severe symptoms of the infection or COVID-19.

In another embodiment, a patient treated in accordance with the methods provided herein is a patient experiencing one or more symptoms of COVID-19. Symptoms of COVID-19 include, but are not limited to, body aches (especially joints and throat), fever, nausea, headaches, fatigue, sore throat, and difficulty breathing. In another embodiment, a patient treated in accordance with the methods provided herein is a patient with COVID-19 who does not manifest symptoms of the disease that are severe enough to require hospitalization.

In another embodiment, a patient treated in accordance with the methods provided herein is a patient experiencing one or more symptoms of COVID-19. Symptoms of COVID-19 include, but are not limited to, body aches (especially joints and throat), fever, nausea, headaches, fatigue, sore throat, and difficulty breathing. In another embodiment, a patient treated in accordance with the methods provided herein is a patient with COVID-19 who does not manifest symptoms of the disease that are severe enough to require hospitalization.

In a specific embodiment, a patient treated in accordance with the methods provided herein is a human. In certain embodiments, a patient treated in accordance with the methods provided herein is a human infant. In some embodiments, a patient treated in accordance with the methods provided herein is a human toddler. In certain embodiments, a patient treated in accordance with the methods provided herein is a human child. In other embodiments, a patient treated in accordance with the methods provided herein is a human adult. In some embodiments, a patient treated in accordance with the methods provided herein is an elderly human. In certain embodiments, a patient treated in accordance with the methods provided herein is patient that is pregnant. As used herein, the term "human adult" refers to a human that is 18 years or older. As used herein, the term "human child" refers to a human that is 1 year to 18 years old. As used herein, the term "human infant" refers to a newborn to 1 year old human. As used herein, the term "human toddler" refers to a human that is 1 years to 3 years old. As used herein, the term "elderly human" refers to a human that is 65 years old and older.

In some embodiments, a patient treated in accordance with the methods provided herein is a patient infected by a virus (e.g., an RNA virus, such as SARS-CoV-2) with a condition that increases susceptibility to virus (e.g., the RNA virus, such as SARS-CoV-2) complications or for which virus (e.g., the RNA virus, such as SARS-CoV-2) increases complications associated with the condition are, e.g., conditions that affect the lung, such as cystic fibrosis, asthma, chronic obstructive pulmonary disease, emphysema, or bacterial infections; cardiovascular disease; or diabetes. Other conditions that may increase virus (e.g., an RNA virus, such as SARS-CoV-2) complications include kidney disorders; blood disorders (including anemia or sickle cell disease); or weakened immune systems (including immunosuppression caused by medications, malignancies such as cancer, organ transplant, or HIV infection). In some embodiments, a patient treated in accordance with the methods provided herein is any subject with a virus (e.g., an RNA virus, such as SARS-CoV-2) infection who is immunocompromised or immunodeficient.

In certain embodiments, patients treated in accordance with the methods provided herein are patients already being treated with antibiotics, antivirals, antifungals, or other biological therapy/immunotherapy.

4.3 Kits

In another aspect, provided herein is a pharmaceutical pack or kit comprising one or more containers filled with a composition (e.g., a pharmaceutical compositions) described herein. In a specific embodiment, provided herein is a pharmaceutical pack or kit comprising one or more containers filled with Rigosertib. Optionally associated with such container(s) can be a notice in the form prescribed by a governmental agency regulating the manufacture, use or sale of pharmaceuticals or biological products, which notice reflects approval by the agency of manufacture, use or sale for human administration. The kits encompassed herein can be used in the above methods.

5. Example 1: Inhibition of SARS-CoV-2 Replication by Rigosertib

Methods: 2,000 Vero E6 cells were seeded into 96-well plates in DMEM (10% FBS) and incubated for 24 h at 37 C, 5% $CO_2$. Two hours before infection, the medium was replaced with 100 μl of DMEM (2% FBS) containing the compound of interest at concentrations 50% greater than those indicated, including a DMSO control. Plates were then transferred into the Biosafety Level 3 (BSL3) facility and 100 PFU (MOI 0.025) was added in 50 μl of DMEM (2% FBS), bringing the final compound concentration to those indicated in FIG. 2. Plates were then incubated for 48 h at 37° C. After infection, supernatants were removed and cells were fixed with 4% formaldehyde for 24 hours prior to being removed from the BSL3 facility. The cells were then immunostained for the viral NP protein with a DAPI counterstain. Infected cells (488 nM) and total cells (DAPI) were quantified using the Celigo (Nexcelcom) imaging cytometer. Percent infection was quantified as ((Infected cells/Total cells)–Background)*100 and the DMSO control was then set to 100% infection for analysis. The $IC_{50}$ and $IC_{90}$ for each experiment were determined using the Prism (Graph-Pad Software) software. For select inhibitors, infected supernatants were assayed for infectious viral titer using the $TCID_{50}$ method. Cytotoxicity was also performed using the MTT assay (Roche), according to the manufacturer's instructions. Cytotoxicity was performed in uninfected VeroE6 cells with same compound dilutions and concurrent with viral replication assay.

$TCID_{50}$ Assay: Infectious supernatants were collected at 48 h post infection and frozen at –80° C. until later use. Infectious titers were quantified by limiting dilution titration on Vero E6 cells. Briefly, Vero E6 cells were seeded in 96-well plates at 20,000 cells/well. The next day, SARS-CoV2-containing supernatant was applied at serial 10-fold dilutions ranging from $10^{-1}$ to $10^{-6}$ and, after 5 days, viral CPE was detected by staining cell monolayers with crystal violet. Median tissue culture infectious doses $(TCID_{50})$/mL were calculated using the method of Reed and Muench (L. J. Reed, H. Muench. A simple method of estimating fifty percent endpoint. Am. J. Hyg., 27 (1938), p. 493).

Results: The results of the study are shown in the FIG. 2 given below.

In this study, 2,000 Vero E6 cells were seeded into 96-well plates in DMEM (10% FBS) and incubated for 24 hrs at 37° C., in the presence of 5% $CO_2$. Vero E6 cells used were purchased from ATCC and thus authenticated (VERO C1008 [Vero 76, clone E6, Vero E6] (ATCC® CRL-1586™); tested negative for mycoplasma contamination prior to commencement). Two hours before infection, the medium was replaced with 100 μl of DMEM (2% FBS) containing the compound of interest at concentrations 50% greater than those indicated in the figure, including a DMSO control. Plates were then transferred into the BSL3 facility and 100 PFU (MOI 0.025) was added in 50 μl of DMEM (2% FBS), bringing the final compound concentration to those indicated in FIG. 2. Plates were then incubated for 48 hrs at 37° C. After infection, supernatants were removed and cells were fixed with 4% formaldehyde for 24 hours prior to being removed from the BSL3 facility. The cells were then immunostained for the viral NP protein (anti-sera produced in the Garcia-Sastre lab; 1:10,000) with a DAPI counterstain. Infected cells (488 nM) and total cells (DAPI) were quantified using the Celigo (Nexcelcom) imaging cytometer. Infectivity is measured by the accumulation of viral NP protein in the nucleus of the Vero E6 cells (fluorescence accumulation). Percent infection was quantified as ((Infected cells/Total cells)–Background)*100 and the DMSO control was then set to 100% infection for analysis. The $IC_{50}$ and $IC_{90}$ for each experiment were determined using the Prism (Graph Pad Software) software. For select inhibitors, infected supernatants were assayed for infectious viral titer using the Median Tissue Culture Infectious Dose $(TCID)_{50}$ method. For this, infectious supernatants were collected at 48 h post infection and frozen at –80° C. until later use. Infectious titers were quantified by limiting dilution titration on Vero E6 cells. Briefly, Vero E6 cells were seeded in 96-well plates at 20,000 cells/well. The next day, SARS-CoV-2-containing supernatant was applied at serial 10-fold dilutions ranging from $10^{-1}$ to $10^{-6}$ and, after 5 days, viral CPE was detected by staining cell monolayers with crystal violet. $TCID_{50}$/mL were calculated using the method of Reed and Muench. Cytotoxicity was also performed using the MTT assay (Roche), according to the manufacturer's instructions. Cytotoxicity was performed in uninfected VeroE6 cells with same compound dilutions and concurrent with viral replication assay. All assays were performed in biologically independent triplicates.

Results from these studies shown in FIG. 2 demonstrate that rigosertib had little or no effect on the viability of Vero E6 cells. In this assay ON123300, a CDK4/ARK5 inhibitor was used as a negative control, which showed no effect on viral replication (Data not shown). Hydroxy-Chloroquine and Remdesivir were used as positive controls and these compounds inhibited the replication of SARS-CoV-2 with an $IC_{50}$ of 733 nM and 826 nM respectively. In these assays, Rigosertib inhibited the replication of SARS-CoV-2 with an $IC_{50}$ of 16 nM suggesting that it is approximately 50-fold more effective than Remdesivir, the only drug currently used for the treatment of COVID-19 patients.

The foregoing is not to be limited in scope by the specific embodiments described herein. Indeed, various modifications of the methods provided herein and their equivalents, in addition to those described herein will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

What is claimed is:

1. A method for treating a SARS-COV-2 infection or COVID-19, comprising administering to the subject an effective amount of Rigosertib to a human subject in need thereof.

2. The method according to claim 1, wherein the rigosertib is administered at a dosage of 280 mg, 560 mg, 840 mg or 1120 mg.

3. The method according to claim 2, wherein the rigosertib dosage is administered once or twice per day.

4. The method according to claim 3, wherein the rigosertib dosage is administered once per day.

\* \* \* \* \*